(12) United States Patent
Chung

(10) Patent No.: US 7,435,417 B2
(45) Date of Patent: Oct. 14, 2008

(54) **PHARMACEUTICAL COMPOSITION CONTAINING DISRUPTED CELL SUSPENSION OF *MONILIA ALBICANS* AND EUGLOBULIN AND METHOD OF TREATING ANIMALS INFECTED WITH CANINE DISTEMPER VIRUS OR ANIMALS HAVING NEUROLOGICAL DISORDERS BY USING THE SAME**

(76) Inventor: Sin Chung, 402, Samsung Art, 945-16, Bangbae 2-dong, Seocho-gu, Seoul 137-062 (KR)

( * ) Notice: Subject to any disclaimer, the term of this patent is extended or adjusted under 35 U.S.C. 154(b) by 42 days.

(21) Appl. No.: 11/486,885

(22) Filed: Jul. 14, 2006

(65) Prior Publication Data

US 2006/0252092 A1    Nov. 9, 2006

Related U.S. Application Data

(63) Continuation-in-part of application No. 10/816,067, filed on Mar. 31, 2004, now abandoned.

(30) Foreign Application Priority Data

Dec. 23, 2003  (KR) .................. 10-2003-0095733

(51) Int. Cl.
*A61K 39/00* (2006.01)
*A61K 45/00* (2006.01)

(52) U.S. Cl. ............... 424/184.1; 424/274.1; 424/278.1
(58) Field of Classification Search .................. None
See application file for complete search history.

(56) References Cited

OTHER PUBLICATIONS

Definition "euglobulin", The On-line Medical Dictionary, cancerweb.ncl.ac.uk/omd/ (2003).*
Heesen et al., "Cloning of the Mouse Fusin Gene, Homologue to a Human HIV-1 Co-factor," The Journal of Immunology, vol. 157 No. 12, pp. 5455-5460 (Dec. 1996).*

* cited by examiner

*Primary Examiner*—Zachariah Lucas
(74) *Attorney, Agent, or Firm*—Abelman, Frayne & Schwab

(57) ABSTRACT

Disclosed is a pharmaceutical composition which comprises a disrupted cell suspension of *Monilia albicans* and euglobulin as effective ingredients, wherein the disrupted cell suspension of the *Monilia albicans* is prepared by culturing the *Monilia albicans* in a liquid culture medium, centrifuging the resulting culture fluid, recovering the supernatant and disrupting the collected cells, and mixing the supernatant and the cell lysate after inactivation, wherein the culture fluid contains the *Monilia albicans* of about $1.2 \times 10^9$ cfu/ml. Also, the present invention discloses a method of treating animals infected with canine distemper virus or animals with neurological disorders.

3 Claims, 1 Drawing Sheet

PHARMACEUTICAL COMPOSITION CONTAINING DISRUPTED CELL SUSPENSION OF *MONILIA ALBICANS* AND EUGLOBULIN AND METHOD OF TREATING ANIMALS INFECTED WITH CANINE DISTEMPER VIRUS OR ANIMALS HAVING NEUROLOGICAL DISORDERS BY USING THE SAME

CROSS REFERENCE TO RELATED APPLICATIONS

This application is a Continuation-in-Part of application Ser. No. 10/816,067, filed 31 Mar. 2004 now abandoned, which claims the priority of Korean Application No. 10-2003-CO95733, filed 23 Dec. 2003.

TECHNICAL FIELD

The present invention relates to a pharmaceutical composition containing a disrupted cell suspension of a fungus, *Monilia albicans*, and euglobulin as effective ingredients and a method of treating animals infected with a canine distemper virus or animals with neurological disorders. The euglobulin is contained in the pharmaceutical composition in an amount of 10 to 250 mg per ml of the disrupted cell suspension of *M. albicans*. The pharmaceutical composition is useful for treating animals infected with the canine distemper virus as well as animals with neurological disorders.

BACKGROUND ART

Canine distemper is a common viral infection among domestic dogs, which is caused by the canine distemper virus and occurs as a highly infectious, acute or subacute febrile disease. The disease produces high morbidity and mortality (Bush Mitchell, Montali R J, Brownstein D, James A E, Appel M J G. Vaccine-induced canine distemper in lesser panda. JAVMA 1976, 169:959-960).

Canine distemper virus (CDV) belongs to the genus Morbillivirus that is part of the family Paramyxovirus (Pringle C R, Paramyxoviridae, Classification and nomenclature of viruses. Arch Virol, 1992, 242-246).

CDV is a negative single-stranded RNA virus, and the genome consists of about 16,000 nucleotides (Bernard N F, David N K and Peter M H, Fields virology 3rd ed. Lippincott Raven Publishers, Philadelphia, 1996, 1177-1204).

CDV has a spherical or filamentous shape and a size ranging from 100 to 700 nm, and contains three nucleocapsid-associated proteins:, nucleocapsid protein (NP), phosphoprotein (P) and large protein (L). The distemper virus further contains matrix protein (M), fusion protein (F) and attachment protein (H) (Appel MJCT, Canine distemper virus, In: Virus infections of carnivors. Elsevier Science Publisher, Amsterdam, 1987, 1:133-159).

Infection with CDV occurs mainly through the respiratory route. After being ingested macrophages in the respiratory tract, the inhaled virus is carried to local lymph nodes by the macrophages and, within several days, spreads to all the lymphatic tissues while causing necrosis in the lymphatic tissues, thereby resulting in immuno-suppression and demyelinating encephalitis leading to epileptiform convulsion (Cornwell H J C, Thomson H, McCandlish I A P, Macartney L and Nash A S, 1988, Encephalitis in dogs associated with a batch of canine distemper (Rockborn) vaccine, Veterinary record, 112:54-59).

Canine distemper is characterized by a variety of clinical signs. In the first stage of CDV, four to six days after exposure to CDV, a fever of up to 39.5° C. to 41.0° C. develops along with depression, anorexia and oculo-nasal discharge. However, these symptoms disappear after two or three days. In the second stage of CDV that begins at two to fourteen days after the fever subsides caused by the viral infection, the fever recurs, which is accompanied by other clinical signs. The most predominant in the second stage are catarrhal symptoms in gastrointestinal and/or respiratory mucous membranes, often along with signs of brain involvement.

The gastrointestinal signs include loss of appetite and vomiting, while the respiratory signs include dry nose, sneezing, mucoid or mucopurulent nasal discharge, coughing and difficulty breathing. The urinary signs include renal pain resulting from nephritis. The major neurological signs are CNS signs resulting from non-suppurative encephalitis. The neurological sings such as hyperesthesia, epileptic fit, circling and paroxysm occur in a seizure-like manner. The seizures develop for a short time several times a day. Also, the frequency of the seizures increases as the disease progresses.

Conventionally, the fever was suppressed by the use of an antipyretic, an immunomodulator (e.g., zymosol, B.S.K), etc. However, such therapy was demonstrated to be ineffective, and clinical symptoms became more severe by remittent fever. In this case, most dogs died from neurological complications such as seizures. On the other hand, the immune serum therapy in which an immune serum is intravenously drip-infused at a mixed state with 5% glucose or directly intravenously administered has an effect of alleviating the early symptoms of the measles. However, after four or five days, the disease recurs very frequently, and, in this case, the immune serum therapy is not effective. In addition, if the immune serum contains blood-derived impurities by incomplete centrifugation, the immune serum therapy may cause animals treated to fall into a coma, and thus, has an unsatisfactory treatment success rate of about 20%. In particular, if the animals develop neurological signs, the above methods no longer have therapeutic efficacy, and thus, the animals eventually die.

Therefore, there is a need for the development of therapeutic agents capable of effectively alleviating the symptoms during the whole CMV infection period ranging from the early phase to the terminal phase.

DISCLOSURE OF THE INVENTION

Keeping in mind the problems encountered in the prior art, the present invention aims to provide a pharmaceutical composition containing a disrupted cell suspension of *Monilia albicans* and euglobulin as effective ingredients, which has high therapeutic efficacy on the symptoms of canine distemper, which ranges from the clinical signs in the early phase to the neurological signs in the terminal phase.

It is another object of the present invention to provide a method of treating an animal infected with a canine distemper virus (CDV) using the pharmaceutical composition.

It is a further object of the present invention to provide a method of treating an animal having a neurological disorder using the pharmaceutical composition.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Figure 1:
FIG. 1 shows an X-ray result of a CDV-infected dog before administration with a pharmaceutical composition according to the present invention.

To achieve the aforementioned objects, in an aspect, the present invention provides a pharmaceutical composition comprising a disrupted cell suspension of a fungus *Monilia albicans* and euglobulin as effective ingredients. Preferably, the disrupted cell suspension of *M. albicans* is prepared by culturing a fungus *M. albicans* in a liquid culture medium, centrifuging the resulting culture fluid, recovering the supernatant and disrupting the collected cells, and mixing the supernatant and the cell lysate after inactivation. Herein, the fungal culture achieve a final concentration of about $1.2 \times 10^9$ cfu/ml. The *M. albicans* fungus is available from Inbionet Co. Ltd., or microbiology laboratories maintaining the fungus.

According to the present invention, the euglobulin is obtained from sera of healthy dogs, for example, by adding an ammonium sulfate solution to canine sera to precipitate euglobulin and purifying the euglobulin two times with saturated ammonium sulfate. The euglobulin is also commercially available, for example, from Dae-Sung Microbiological Labs. Co. Ltd. (Uiwang-si, Gyeonggi-do, Korea).

The euglobulin is preferably contained in the pharmaceutical composition in an amount of 10 to 250 mg per ml of the disrupted cell suspension of *M. albicans*. When the euglobulin content is outside this range, the therapeutic efficacy thereof decreases.

In another aspect, the present invention provides a method of treating an animal infected with a canine distemper virus (CDV) using the pharmaceutical composition. The pharmaceutical composition is preferably administered to the CDV-infected animal prior to development of neurological signs in a dose of 0.3 to 0.6 ml per kg body weight three times daily. The administration is preferably carried out via the subcutaneous route. In addition, the pharmaceutical composition may be administered in combination with a stomach protectant and an antibiotic. Preferred examples of the stomach protectant include metoclopramide hydrochloride, cimetidine and nuxvomica. The stomach protectant is subcutaneously administered in a dose of 0.2 to 0.3 ml/kg twice, and preferably, once daily. Examples of the antibiotic include sulfa drugs, cepha drugs, enrofloxacin, penicillin and ampicillin. The antibiotics are rotated in use, and subcutaneously or intramuscularly administered in a dose of 0.3 to 0.45 ml/kg twice, and preferably, once daily.

When a CDV-infected animal develops neurological signs such as seizures, ataxia, hyperesthesia, cerebral tremor, paroxysm and epileptic fit, the pharmaceutical composition may be subcutaneously injected into the animal in a dose of up to 2 ml/kg. In addition, when the neurological signs are accompanied by a high fever, the dose of the pharmaceutical composition may be gradually increased up to 3 ml/kg.

When the body temperature decreases to less than 38° C. post-treatment, the frequency of the administration of the pharmaceutical composition may be reduced from three times to twice, and finally once per day.

In addition to animals infected with CDV, the pharmaceutical composition of the present invention has excellent therapeutic efficacy on animals having neurological disorders, such as cerebral apoplexy, brain injury, neurological dysfunctions, Alzheimer's and myoclonus.

In case of treating animals having neurological disorders, the pharmaceutical composition of the present invention is preferably administered to the animals in a dose of 0.3 to 0.6 ml per kg body weight once daily. The administration is preferably carried out via the subcutaneous route. In addition, the pharmaceutical composition may be administered in combination with a stomach protectant and an antibiotic. Preferred examples of the stomach protectant include metoclopramide hydrochloride, cimetidine and nuxvomica. The stomach protectant is subcutaneously administered in a dose of 0.2 to 0.3 ml/kg twice, and preferably, once daily. Examples of the antibiotic include sulfa drugs, cepha drugs, enrofloxacin, penicillin and ampicillin. The antibiotics are rotated in use, and subcutaneously or intramuscularly administered in a dose of 0.3 to 0.45 ml/kg twice, and preferably, once daily.

The present invention will be explained in more detail with reference to the following examples in conjunction with the accompanying drawings. However, the following examples are provided only to illustrate the present invention, and the present invention is not limited to the examples.

EXAMPLE 1

Culturing of *M. albicans* and Preparation of a Disrupted Cell Suspension of *M. albicans*

A fungus *Monilia albicans* was maintained on YM solid medium. Liquid culture was carried out, as follows. An inoculum of the fungus was inoculated in an optimized SMY liquid medium at a concentration of 3% (v/v), and cultured at 28° C. for 42 hrs under a pH of 4.5. The resulting culture fluid was found to contain *M. albicans* of about $1.2 \times 10^9$ cfu/ml. Then, the culture fluid was incubated at 120° C. for 20 min to kill the cultivated fungus.

The culture fluid of 33 L, containing *M. albicans*, was centrifuged. The supernatant was recovered, while the cell pellet was washed and resuspended in saline. Then, the cells were passed three times through a cell disrupter (Cell Disruption System Model Z-Plus 4 kw, Constant System Ltd.) under a pressure of 25 KPSI. The cell lysate of 3,000 ml was inactivated with 0.3% formalin at 37° C. for three days. Also, the centrifugal supernatant of 32,000 ml was inactivated with 0.3% formalin at 37° C. for three days.

The inactivated cell lystate of 3,000 ml was mixed with the inactivated centrifugal supernatant of 32,000 ml, thus yielding a disrupted cell suspension of *M. albicans*.

The *M. albicans*: a gift from the Inbionet Co. Ltd

The SMY medium (1 L): 10 g malt extract, 3 g yeast extract, 30 g sucrose, 3 g $(NH_4)_2SO_4$, 2 g $KH_2PO_4$, 0.5 g $MgSO_4.7H_2O$, pH 4.5

EXAMPLE 2

Test for Microbiological Contamination and Safety of the Disrupted Cell Suspension of *M. albicans*

The disrupted cell suspension of *M. albicans* was subjected to a microbiological contamination test for eight days, and found to be not contaminated with any microorganism. In addition, the disrupted cell suspension of *M. albicans* was evaluated for safety for eight days under the condition listed in Table 1, below, and, as a result, was found to be safe.

TABLE 1

Safety test and result (mouse test)

| Administration | Dose (ml) | Tested mouse No. | Dead mouse No. | Survived mouse No. | Viability |
| --- | --- | --- | --- | --- | --- |
| Intraperitoneal | 0.5 | 5 | 0 | 5 | 100% |
| Intraperitoneal | 1.0 | 5 | 0 | 5 | 100% |
| Subcutaneous | 0.5 | 5 | 0 | 5 | 100% |
| Subcutaneous | 1.0 | 5 | 0 | 5 | 100% |

EXAMPLE 3

Preparation of Pharmaceutical Compositions According to the Present Invention

The disrupted cell suspension of *M. albicans* prepared in Example 1 was mixed with euglobulin (50 mg/ml, Dae-Sung Microbiological Labs. Co. Ltd., Uiwang-si, Gyeonggi-do, Korea), which was isolated and purified from canine sera, injectable physiological saline and an injectable preservative (Thimerosal), based on the compositions listed in Table 2, below, thereby generating pharmaceutical compositions.

TABLE 2

Composition of the pharmaceutical compositions according to the present invention

|  | Pharmaceutical compositions | | |
| --- | --- | --- | --- |
|  | A | B | C |
| Disrupted cell suspension of *M. albicans* | 10 ml | 10 ml | 10 ml |
| Euglobulin | 100 mg | 500 mg | 2500 mg |
| NaCl | 0.85% | 0.85% | 0.85% |
| Thimerosal | 0.01% | 0.01% | 0.01% |

The euglobulin was used in an amount of 10 to 250 mg per ml of the disrupted cell suspension of *M. albicans*.

EXAMPLE 4

Evaluation of Therapeutic Efficacy of the Pharmaceutical Composition According to the Present Invention on Animals Infected with CDV (1) Administration of the Pharmaceutical Composition B to Dogs Infected with CDV Twenty dogs infected with CDV were subcutaneously administered with the pharmaceutical composition B prepared in Example 3 in a dose of 0.3 to 2 ml/kg three times daily for 15 days. Herein, a higher dose was administered to dogs developing severe symptoms. After the administration began, when the body temperature decreased to less than 38° C., the administration frequency of the pharmaceutical composition was reduced from three times to twice, and finally once per day. Also, during the administration of the pharmaceutical composition B, a stomach protectant, cimetidine, was subcutanesouly injected into the dogs once daily in a dose of 0.3 ml/kg. Further, in a rotary manner, antibiotics including sulfa drugs, cepha drugs, enrofloxacin, penicillin and ampicillin were subcutanesouly injected into the dogs once daily in a dose of 0.4 ml/kg.

(2) Blood Analysis of the CDV-Infected Dogs Before the Administration with the Pharmaceutical Composition B Before the administration with the pharmaceutical composition B, the twenty CDV-infected dogs were subjected to a blood test. The results are given in Table 3, below.

TABLE 3

Blood test results

| Tested items | Before treatment | Normal ranges |
| --- | --- | --- |
| Total protein (g/dl) | 4.8 | 5.4-7.4 |
| Albumin (g/dl) | 3.6 | 2.9-4.2 |
| Total bilirubin (mg/dl) | 0.2 | 0.0-0.4 |
| AST (GOT) (u/l) | 44-79 | 15-43 |
| ALT (GPT) (u/l) | 21 | 19-70 |
| CK (CPK) (u/l) | 32-700 | 46-320 |
| RBC (M/μl) | 5.12 | 5.50-8.50 |
| Hb (g/dl) | 10.6 | 12.0-18.0 |
| HCT (%) | 33.7 | 37.0-55 |
| MCV (fL) | 65.9 | 60.0-74.0 |
| MCH (pg) | 20.7 | 19.5-24.5 |
| MCHC (g/dl) | 31.5 | 31.0-36.0 |
| RDW (%) | 20.2 | 12.0-18 |
| PLT (k/μl) | 877 | 200-500 |
| MPV (fL) | 14.0 | 5.0-15.0 |
| WBC | 19.26-60.10 | 6.0-17.0 |
| NE (k/μl) | 17.14-47.13 | 3.0-11.8 |
| LY (k/μl) | 2.90 | 1.0-4.8 |
| MO (k/μl) | 1.34 | 0.2-2.0 |
| EO (k/μl) | 0.71 | 0.1-1.3 |
| BA (k/μl) | 0.24 | 0-0.5 |

In Table 3, mean values obtained from the blood test of the CDV-infected dogs before the administration with the pharmaceutical composition B are listed in the middle column, while normal ranges of the assayed items are listed in the most right column.

Therapeutic efficacy of the pharmaceutical composition B can be evaluated by analyzing levels of AST (GOT), CK (CPK), WBC, NE, etc. The level of CK (CPK) that is a maker for neurological symptoms was found to increase immediately after subcutaneous injection by muscle injury caused by the injection, but to return to within the normal range after the administration period. The number of WBC was slightly reduced first but sharply increased with a left shift. However, after the administration of the pharmaceutical composition B, the blood WBC level rapidly decreased near to the normal range. In the terminal phase of canine distemper, some dogs showed normal WBC levels. In this case, the WBC level was elevated immediately after the administration of the pharmaceutical composition B and then restored to the normal range.

Figure 2:
FIG. 2 shows an X-ray result of the CDV-infected dog that has been administered with the pharmaceutical composition according to the present invention.

Before and after the administration with the pharmaceutical composition B, the dogs were subjected to X-ray analysis. The X-ray results are given FIGS. 1 and 2. FIG. 1 shows X-ray images of a CDV-infected dog before administration with the pharmaceutical composition B, while FIG. 2 shows X-ray images of the CDV-infected dog that has been administered with the pharmaceutical composition B. About ten days after the administration of the pharmaceutical composition B, the hazy region turned clear.

EXAMPLE 5

Comparison of Therapeutic Efficacy on Animals Infected with CDV of the Pharmaceutical Compositions According to the Present Invention and the Conventional Drugs (1) Administration of the Pharmaceutical Composition A to Dogs Infected with CDV but Not Developing Neurological Signs Forty dogs infected with CDV but not developing neurological signs were administered with the pharmaceutical composition A prepared in Example 3 or a conventional immunomodulator.

The forty dogs were divided into four groups each of which consisted of ten dogs. Each group was subcutaneously administered with the pharmaceutical composition A, or zymosol, B.S.K or ultracorn, which are conventionally used. The administration was carried out for 20 days. In case of the pharmaceutical composition A, after the administration began, when the body temperature decreased to less than 38° C., the administration frequency of the pharmaceutical composition was reduced from three times to twice, and finally once, per day. Also, during the administration period, a stomach protectant, metoclopramide hydrochloride was subcutanesouly injected into the dogs once daily in a dose of 0.3 ml/kg. Further, in a rotary manner, antibiotics including sulfa drugs, cepha drugs, enrofloxacin, penicillin and ampicillin were subcutanesouly injected into the dogs once daily in a dose of 0.35 ml/kg.

TABLE 4

Administration scheme to dogs infected with CDV but not developing neurological signs and therapeutic efficacy of the pharmaceutical composition A and the conventional drugs

| | Phar. Comp. A | Zymosol | B.S.K | Ultracorn |
|---|---|---|---|---|
| Administration route | Subcutaneous | Subcutaneous | Subcutaneous | Subcutaneous |
| Dose | 0.6 ml/kg | 0.4 ml/kg | 0.4 ml/kg | 0.5 ml/kg |
| Administration frequency | Once to three times daily | Once daily | Once daily | Once daily |
| Administration period | 20 days | 20 days | 20 days | 20 days |

TABLE 4-continued

Administration scheme to dogs infected with CDV but not developing neurological signs and therapeutic efficacy of the pharmaceutical composition A and the conventional drugs

| | Phar. Comp. A | Zymosol | B.S.K | Ultracorn |
|---|---|---|---|---|
| Tested dog No. | 10 | 10 | 10 | 10 |
| Completely cured dog No. | 8 | 0 | 1 | 1 |
| Cure rate | 80% | 0% | 10% | 10% |

Zymosol: immunoenhancer, purchased from the Shinhan Biochem Company, Korea; per 1 ml: 10 mcg zymosan, 277 mcg cobalt gluconate, 259 mcg copper gluconate, 295 mcg of manganese gluconate, 278 mcg nikel gluconate, 235 mcg zinc gluconate, 78.5 mcg sodium gluconate and 50 mcg glucose
B.S.K: immunoenhancer, purchased from the Samdong Trading Company, Korea; per 1 ml: 200 mcg *Bacillus subtilis* culture
Ultracorn: immunostimulator, purchased from the Virbackorea Company, Korea; per 1 ml: 20 mg Cirynebacterium cutis, which is prepared by complete suspension and then high concentration As shown in Table 4, when dogs were administered with the pharmaceutical composition of the present invention, eight of the ten dogs tested were completely recovered. Unlike to the present composition with a high therapeutic effect of about 80%, the conventional drugs, zymosol, B.S.K and ultracorn were found to have poor therapeutic effects of 0%, 10% and 10%, respectively.

(2) Administration of the Pharmaceutical Composition C to Dogs Developing Neurological Signs Forty dogs with neurological symptoms were administered with the pharmaceutical composition C prepared in Example 3 or a conventional immunomodulator (zymosol, B.S.K or ultracorn).

The forty dogs were divided into four groups each of which consisted of ten dogs. Each group was subcutaneously administered with the pharmaceutical composition A, zymosol, B.S.K or ultracorn. The administration was carried out for 20 days. In case of the pharmaceutical composition A, after the administration began, when the body temperature decreased to less than 38° C., the administration frequency of the pharmaceutical composition was reduced from three times to twice, and finally once, per day. Also, during the administration period, a stomach protectant, nuxvomica was subcutanesouly injected into the dogs twice daily in a dose of 0.3 ml/kg. Further, in a rotary manner, antibiotics including sulfa drugs, cepha drugs, enrofloxacin, penicillin and ampicillin were subcutanesouly injected into the dogs twice daily in a dose of 0.35 ml/kg.

TABLE 5

Administration scheme to the dogs with neurological signs and therapeutic efficacy of the pharmaceutical composition C and the conventional drugs

| | Phar. Comp. C | Zymosol | B.S.K | Ultracorn |
|---|---|---|---|---|
| Administration route | Subcutaneous | Subcutaneous | Subcutaneous | Subcutaneous |
| Dose | 0.8 ml/kg | 0.4 ml/kg | 0.4 ml/kg | 0.5 ml/kg |
| Administration frequency | Once to three times daily | Once daily | Once daily | Once daily |
| Administration period | 20 days | 20 days | 20 days | 20 days |
| Tested dog No. | 10 | 10 | 10 | 10 |

TABLE 5-continued

Administration scheme to the dogs with neurological signs and therapeutic efficacy of the pharmaceutical composition C and the conventional drugs

|  | Phar. Comp. C | Zymosol | B.S.K | Ultracorn |
|---|---|---|---|---|
| Completely cured dog No. | 7 | 0 | 0 | 0 |
| Cure rate | 70% | 0% | 0% | 0% |

As shown in Table 5, when administered with the pharmaceutical composition C of the present invention, seven of ten dogs were completely cured. When administered with the conventional drugs, the neurological symptoms were alleviated at the initial stage of the administration period, but recurred seven to ten days after the administration began, resulting in death of all of the tested dogs. This recurrent neurological signs are believed to result from the inability of the conventional drugs in stimulating the immune system. On the other hand, during the period of the administration with the conventional drugs, a change in the neurological signs was observed.

EXAMPLE 6

Evaluation of Therapeutic Efficacy of the Pharmaceutical Composition according to the Present Invention on CDV-infected Dogs with Neurological Symptoms The therapeutic efficacy of the pharmaceutical composition of the present invention on neurological symptoms was further investigated, as follows.

Various time points after developing neurological symptoms, thirty CDV-infected dogs were subcutaneously administered with the pharmaceutical composition B prepared in Example 3 twice daily in a dose of 1.0 ml/kg.

As a result, when the pharmaceutical composition B was administered to the dogs four days after the onset of neurological signs, the neurological signs completely disappeared between three to within ten days after the administration. When pharmaceutical composition B was administered to the dogs between four to seven days after the onset of neurological signs, the neurological signs gradually disappeared between ten to fifteen days after the administration. However, in the later case, mild neurological signs remained. When the pharmaceutical composition B was administered to the dogs after seven days after the onset of neurological signs, the neurological signs were slowly alleviated after twenty days after the administration. However, in this case, mild neurological signs remained.

EXAMPLE 7

Evaluation of Therapeutic Efficacy of the Pharmaceutical Composition According to the Present Invention on Animals with Neurological Disorders such as Cerebral Apoplexy, Brain Injury, Neurological Dysfunctions, Alzheimer's and Myoclonus 25 dogs with brain injuries, neurological dysfunctions, Alzheimer's disease and myoclonus, which were caused by cerebral apoplexy or a traffic accident, were subcutaneously administered with the pharmaceutical. composition B prepared in Example 3 once daily in a dose of 0.3 ml/kg. The administration was carried out for about 15 days. The pathological symptoms began to be alleviated between three to five days after the administration. For example, strong appetite, inability to recognize their owner, abnormal behavior in urination and evacuation, inability to stand upright or coma was found to be alleviated.

EXAMPLE 8

Evaluation of the Effects of the Pharmaceutical Composition According to the Present Invention on Blood CDV and Antibody Titers Six Beagles, which had no persisting maternal antibodies against CDV, were challenged with a domestic isolate of CDV, Seoul 98 thymus emulsion, via the jugular vein, and monitored for clinical signs of canine distemper. Blood samples were collected on the challenge day and 2, 6, 8, 10, 12, 14 and 20 days after the challenge, and were evaluated for blood virus and antibody titer using IgM distemper kit (Immunocomb, seoul, Korea). The results are given in Table 6, below. Viremia was detected between day 2 and day 6 in most individuals. When the composition of the present invention was administered (dosage: 0.30 ml/kg) upon the emergence of CDV in the blood, it prevented a rapid increase in antibody titer against CDV in test groups. Upon CDV infection, antibody titers against CDV usually rapidly increase, leading to the death of CDV-infected dogs. The administration of the present composition resulted in a slow increase in such antibody titers with no viremia. Thus, clinical signs of death disappeared.

TABLE 6

Changes in the emergence of CDV and antibody titers against CDV in the blood

| Group No. | D-0 | D-2 | D-4 | D-6 | D-8 | D-10 | D-12 | D-14 | D-16 | D-18 | D-20 |
|---|---|---|---|---|---|---|---|---|---|---|---|
| 1 (Control) | 3 | 6 | 6 | 6 | 6 | Dead | | | | | |
| 2 (Test group) | 0 | 0 | 0 | 0 | 2 | 4 | 3 | Dead | | | |
| 3 (Test group) | 3 | 3 | 3 | 3 | 3 | 3 | 4 | 4 | 2 | 5 | 5 |
| 4 (Test group) | 0 | 3 | 3 | 3 | 6 | 2 | 0 | 0 | Dead | | |
| 5 (Test group) | 2 | 0 | 4 | 6 | 4 | 4 | 4 | 4 | 4 | 3 | 4 |
| 6 (Test group) | 2 | 2 | 2 | 1 | 2 | 0 | 2 | 3 | 3 | 2 | 4 |

Note:
Numerals in bold indicate the emergence of CDV in the blood

EXAMPLE 9

Evaluation of the Effects of the Pharmaceutical Composition According to the Present Invention on CDV in the Blood Four Beagles, which had no persisting maternal antibodies against CDV, were challenged with a domestic isolate of CDV, Seoul 98 thymus emulsion, via the jugular vein, and monitored for clinical signs of canine distemper. Blood samples were collected on the challenge day and 3, 8, 10, 14, 18, 22, 25, 28 and 32 days after the challenge, and were evaluated for blood virus titer. The present composition was administered (dosage: 0.50 ml/kg) upon the emergence of CDV. The results are given in Table 7, below. Viruses appeared on post-challenge day 3 or 14 in the test groups. In cases where the present composition was administered at that time, viruses could no longer be detected in the blood within 10 to 15 days.

TABLE 7

| Group No. | The emergence of CDV in the blood ||||||||||
|---|---|---|---|---|---|---|---|---|---|---|
| | D-0 | D-3 | D-8 | D-10 | D-14 | D-18 | D-22 | D-25 | D-28 | D-32 |
| 1 (Control) | − | − | − | − | + | + | + | + | + | + |
| 2 (Test group) | − | − | − | − | + | + | + | + | − | − |
| 3 (Test group) | − | − | − | − | + | + | + | + | + | − |
| 4 (Test group) | − | + | + | + | + | + | − | − | − | − |

INDUSTRIAL APPLICABILITY

As described hereinbefore, the pharmaceutical composition of the present invention has a therapeutic effect of about 70% to 80% on CDV-infected dogs, and such a therapeutic effect can be achieved immediately after its administration. In particular, unlike to the conventional drugs with no therapeutic effect on CDV-infected animals with neurological symptoms, the pharmaceutical composition of the present invention has a high therapeutic effect of about 70% on the animals. In addition, the pharmaceutical composition has therapeutic efficacy on animals with neurological disorders cause of which does not have been identified.

The invention claimed is:

1. A pharmaceutical composition for treating canine distemper, comprising:

a disrupted cell suspension of *Monilia albicans*, in which *Monilia albicans* cells are disrupted and inactivated; and euglobulin from canine sera in an amount ranging from 10 mg to 250 mg per ml of the disrupted cell suspension of the *Monilia albicans*.

2. The pharmaceutical composition for treating canine distemper as set forth in claim 1, wherein the disrupted cell suspension of the *Monilia albicans* is prepared by culturing the *Monilia albicans* in a liquid culture medium, centrifuging the resulting culture fluid, recovering a supernatant and disrupting and inactivating collected cells, and mixing the supernatant and the inactivated cell lysate, wherein the culture fluid contains the *Monilia albicans* in an amount of about $1.2 \times 10^9$ cfu/ml.

3. The pharmaceutical composition for treating canine distemper as set forth in claim 1, wherein the canine-derived euglobulin is prepared by adding ammonium sulfate to sera from healthy dogs to precipitate euglobulin and isolating and purifying the euglobulin two times with saturated ammonium sulfate.

* * * * *